United States Patent [19]

Kubota

[11] Patent Number: 4,937,348
[45] Date of Patent: Jun. 26, 1990

[54] PROCESS FOR PREPARING 2,2'-METHYLENE-BIS-(4-HYDROCARBYL-6-BENZOTRIAZOLYLPHENOLS)

[75] Inventor: Naohiro Kubota, Saitama, Japan

[73] Assignee: Adeka Argus Chemical Co., Ltd., Urawa, Japan

[21] Appl. No.: 138,998

[22] Filed: Dec. 29, 1987

Related U.S. Application Data

[63] Continuation of Ser. No. 795,385, Nov. 6, 1985, abandoned.

[30] Foreign Application Priority Data

Nov. 9, 1984 [JP] Japan .................. 59-236290

[51] Int. Cl.$^5$ .............................................. C08K 5/34
[52] U.S. Cl. ...................................... 548/259; 548/260
[58] Field of Search .................. 548/260, 257, 259; 568/727, 722

[56] References Cited

U.S. PATENT DOCUMENTS

| | | | |
|---|---|---|---|
| 2,033,092 | 3/1936 | Bruson | 528/163 |
| 2,839,586 | 6/1958 | Fritz | 568/722 |
| 3,055,862 | 9/1962 | Berkley et al. | 548/727 |
| 3,936,305 | 2/1976 | Hiraishi et al. | 548/260 |
| 4,681,905 | 7/1987 | Kubota | 548/260 |

OTHER PUBLICATIONS

March, Adv. Org. Chem., 2nd ed. (McGraw-Hill, New York) p. 502 (1977).
Decombe, Chem. Abs., vol. 32, entry #1009 (5) (1938).
Rohm and Haas, *Alkylphenols* (a publication of Rohm and Haas Co., Philadelphia, (1960).
DeCombe, Acad des Sciences–Comptes Rendus, vol. 196, pp. 866–868 (1933).
Seebach, Chem. Abs. 32:1009(5) (1938).
Scheiber, Chem. Abs. 31:4742(8) (1937).

*Primary Examiner*—Mukund J. Shah
*Assistant Examiner*—Andrew G. Rozycki

[57] ABSTRACT

A process is provided for preparing 2,2'-methylene-bis-(4-hydrocarbyl-6-benzotriazolyl-phenols) having formula III:

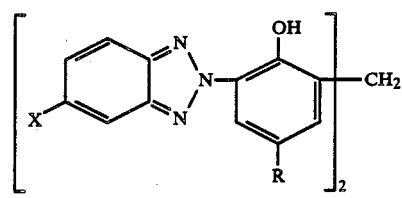

wherein:
R is selected from the group consisting of alkyl having from one to about twelve carbon atoms; arylalkyl having from seven to about fourteen carbon atoms and cycloalkyl having from three to about twelve carbon atoms;
X is selected from the group consisting of hydrogen, halogen, alkyl having from one to about twelve carbon atoms, aryl having from six to ten carbon atoms, arylalkyl having from seven to about sixteen carbon atoms, alkoxy having from one to about twelve carbon atoms, aryloxy having from six to ten carbon atoms; and arylalkoxy having from seven to about sixteen carbon atoms;
$R_1$ and $R_2$ are selected from the group consisting of hydrogen; alkyl having from one to about six carbon atoms, and $R_1$ and $R_2$ taken together to form a four to six member heterocyclic ring including a nitrogen atom; provided, that at least one of $R_1$ and $R_2$ is not hydrogen; comprising (1) reacting a 4-hydrocarbyl-6-benzotriazolyl phenol having the formula I:

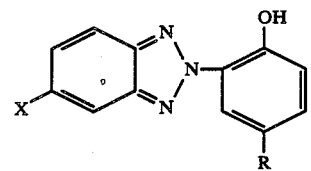

with an amine $HNR_1R_2$ and formaldehyde in an organic solvent to produce a Mannich base having formula II:

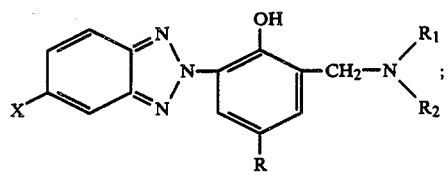

(2) reacting the Mannich base with itself or a 4-hydrocarbyl-6-benzotriazolyl phenol having formula I, thereby forming a 2,2'-methylene-bis-(4-hydrocarbyl-6-benzotriazolyl-phenol of formula III.

25 Claims, No Drawings

PROCESS FOR PREPARING 2,2'-METHYLENE-BIS-(4-HYDROCARBYL-6-BENZOTRIAZOLYLPHENOLS)

This is a continuation of application Ser. No. 795,385, filed Nov. 6, 1985, now abandoned.

2,2'-Methylene-bis-(4-hydrocarbyl-6-benzotriazolylphenols) are known light stabilizers for plastics, and a process for preparing them is disclosed in *Chemical Abstracts* 74 53666f (1971). The corresponding 2-(2-hydroxy-5-alkylphenyl) benzo triazole is reacted with formaldehyde in sulfuric acid, and a 99% yield is claimed.

*Chemical Abstracts* 74 53666f discloses reacting the diazonium salt from ortho-nitro aniline with the corresponding methylene bis phenol in aqueous sodium hydroxide/sodium carbonate solution, and then reacting with zinc powder and sodium hydroxide/sodium thiosulate, yielding on acidification the 2,2'-methylene-bis-(4-hydrocarbyl-6-benzotriazolyl phenol).

U.S. Pat. No. 3,936,305, patented Feb. 3, 1976, to Hiraishi, Futaki, Horii and Yamashita, discloses a group of alkylidene-bis-benzotriazolyl phenols having the formula:

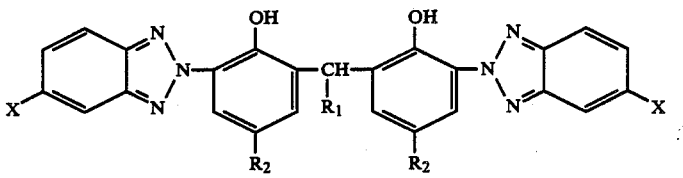

wherein $R_1$ is an alkyl group having 1 to 13, preferably 5 to 13 carbon atoms, $R_2$ is an alkyl group having 1 to 18 carbon atoms and X is hydrogen, a halogen, an alkyl, an alkoxy, an aryloxy, an aralkyloxy or an aryl group.

These compounds are prepared by a synthesis illustrated for 2,2'-octylidene-bis(4-methyl-6-(5"-methylbenzotriazolyl)-phenol)).

Dried hydrogen chloride is introduced into a benzene solution containing 129.6 g of p-cresol, 64.1 g of n-caprylaldehyde and 2 ml of n-dodecylmercaptan at room temperature for 4 hours. This is left to stand overnight at room temperature. Thereafter, the reaction liquid is washed with water, washed with 1N aqueous solution of sodium bicarbonate until the wash liquid shows weak acidicity and then again washed with water. After the benzene layer is dried, the solvent is distilled out and the residue is distilled under reduced pressure to obtain a fraction of 165°–175° C./1 Torr. The fraction is recrystallized from n-hexane to obtain white crystal of 2,2'-octylidene bis(4-methylphenol) having a melting point of 107.8°–108.8° C.

Separately, 120 ml of concentrated hydrochloric acid and 40 ml of water are added to 60.8 g of 4-methyl-2-nitroaniline and these are sufficiently stirred. Thereafter, 50 ml of water containing 28.9 g of sodium nitrite is added dropwise thereto at 0° C. over a period of 10 minutes. Furthermore, this is stirred for another 100 minutes and a small amount of sulfamic acid is added thereto and undissolved matter is filtered off to obtain a diazonium solution.

32.6 g of 2,2'-octylidene bis(4-methylphenol) obtained hereinabove is dissolved in a mixed solvent of 300 ml of methyl alcohol and 200 ml of acetone in which 50 g of sodium hydroxide is dissolved. To this solution is added dropwise said diazonium solution with stirring at a temperature of 0°–10° C. After stirring for another 2 hours, glacial acetic acid is added thereto to obtain a pH of 4. Thus obtained oily product is recrystallized from ethanol.

6.5 g of this 2,2'-octylidene bis(4-methyl-6-(4"-methyl-2"-nitrophenylazo)phenol) is suspended in 100 ml of ethanol and heated to reflux temperature. 50 ml of water containing 8.4 g of sodium hydroxide is added to the suspension and furthermore, 6.5 g of zinc powder is added little by little. Refluxing is further carried out for 1 hour. Thereafter, the zinc powder is filtered out with warm and pH of the filtrate is made 4–5 with 1N hydrochloric acid to separate crystal, which is filtered off. The crystal is recrystallized from ethanol to obtain the 2,2-octylidene-bis-(4-methyl-6-(5"-methyl benzotriazolyl)phenol).

*Chemical Abstracts* 74 53666f (1971) discloses the preparation of methylene bis-(benzotriazolyl phenols) by reacting 2,2'-methylenebis-phenol with an o-nitrodiazonium salt, followed by hydrogenating the resultant azo compound. However, the yield is rather low, and the product contains a monosubstituted impurity.

*Chemical Abstracts* 77 62720h (1972) discloses the preparation of methylene-bis-(benzotriazolyl phenols) by reacting benzotriazolyl phenol with formaldehyde in sulfuric acid. However, the yield in this method is also low, and the reaction conditions are impractical.

In accordance with this invention, a process is provided which enables the preparation of 2,2'-methylene-bis-(4-hydrocarbyl-6-benzotriazolyl-phenols) under mild conditions in high yield.

A 4-hydrocarbyl-6-benzotriazolyl-phenol of formula I is reacted with the corresponding amine $HNR_1R_2$ and formaldehyde in an organic solvent to produce a Mannich base of formula II. The Mannich base is reacted with itself or a 4-hydrocarbyl-6-benzotriazolyl-phenol of formula I, thereby forming the desired 2,2'-methylene-bis-(4-hydrocarbyl-6-benzotriazolyl phenol.

The following is an outline of the reactions in this synthesis:

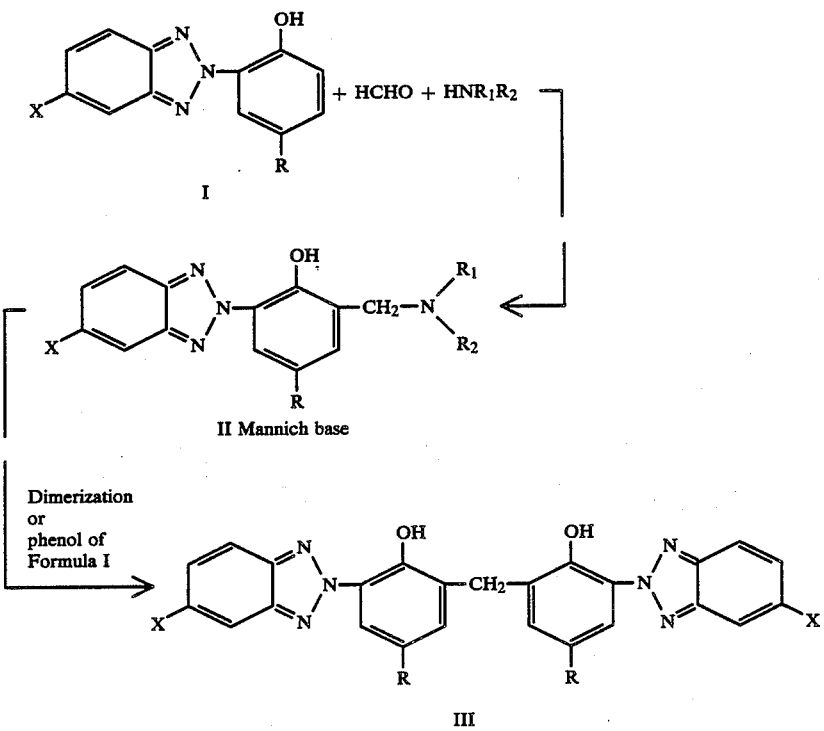

In the above formulae, R is selected from the group consisting of alkyl having from one to about twelve carbon atoms; arylalkyl having from seven to about fourteen carbon atoms and cycloalkyl having from three to about twelve carbon atoms;

X is selected from the group consisting of hydrogen, halogen, alkyl having from one to about twelve carbon atoms, aryl having from six to ten carbon atoms, arylalkyl having from seven to about sixteen carbon atoms, alkoxy having from one to about twelve carbon atoms, aryloxy having from six to ten carbon atoms; and arylalkoxy having from seven to about sixteen carbon atoms;

$R_1$ and $R_2$ are selected from the group consisting of hydrogen; alkyl having from one to about six carbon atoms, and $R_1$ and $R_2$ taken together to form a four to six member heterocyclic ring including a nitrogen atom; provided, that at least one of $R_1$ and $R_2$ is not hydrogen.

The invention accordingly provides a process for preparing alkylidene-bis-benzotriazolyl phenols of Formula III, comprising (1) reacting a 4-hydrocarbyl-6-benzotriazolyl phenol having the formula I:

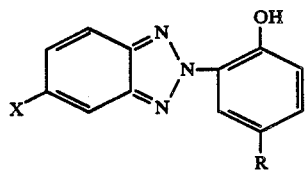

with an amine $HNR_1R_2$ and formaldehyde in an organic solvent to produce a Mannich base having formula II:

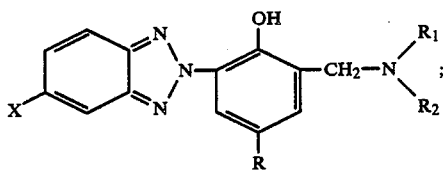

and (2) reacting the Mannich base with itself or a 4-hydrocarbyl-6-benzotriazolyl phenol having formula I, thereby forming a 2,2'-methylene-bis-(4-hydrocarbyl-6-benzotriazolyl-phenol of formula III.

Exemplary R alkyl include methyl, ethyl, propyl, isopropyl, butyl, isobutyl, t-butyl, amyl, isoamyl, hexyl, heptyl, octyl, isooctyl, 2-ethylhexyl, 1,1,3,3-tetramethylbutyl, nonyl, decyl, dodecyl;

Exemplary R arylalkyl include benzyl, α-methylbenzyl, cumyl, phenethyl, phenpropyl, phenbutyl, phenoctyl, trimethyl benzyl, butyl benzyl, hexyl benzyl, dibutyl benzyl;

Exemplary cycloalkyl include cyclopropyl, cyclobutyl, cyclopentyl, cyclohexyl, cycloheptyl, cyclooctyl, and cyclododecyl;

Exemplary X halogen include fluorine, chlorine and bromine, exemplary X alkyl include methyl, ethyl, propyl, isobutyl, isoamyl, and hexyl; exemplary X alkoxy include methoxy, ethoxy, butoxy and octoxy;

Exemplary amine $HNR_1R_2$ include primary alkyl amines such as monomethylamine, monoethylamine, monopropylamine and monobutylamine; secondary alkyl amines such as dimethylamine, diethylamine, di-n-propylamine, diisopropylamine, di-n-butylamine, di-t-butylamine, diisobutylamine, diamylamine, ethylmethylamine and ethyl-isopropylamine; and heterocyclic amines such as morpholine, piperidine and pyrrolidine.

Formaldehyde as such or in any of its polymeric forms can be used in the process of this invention, such as gaseous formaldehyde; aqueous solutions of formaldehyde; paraformaldehyde; trioxane; trioxymethylene; tetraoxymethylene; and other solid polymers of formaldehyde.

Any inert organic solvent that is a solvent for the reactants can be used in this invention, including alkanols such as methanol, ethanol, isopropanol and n-butanol; hydrocarbons such as hexane, heptane, benzene, toluene, xylene, petroleum ethers, and mineral spirits; and cycloaliphatic ethers such as furan, tetrahydrofuran and dioxane. The amount of solvent is not critical, and can suitably be within the range from about 50 to about 500 weight % based on the amount of benzotriazolyl phenol present.

In the reaction of 4-hydrocarbyl-6-benzotriazolyl-phenol of formula (I) with amine and formaldehyde in the organic solvent, the amounts of amine and formaldehyde can be stoichiometric, or slightly less, and preferably each is within the range from about 0.5 to about 1 mole, per mole of 4-hydrocarbyl-6-benzotriazolyl phenol.

The reaction of Mannich base with itself or 4-hydrocarbyl-6-benzotriazolyl-phenol to produce 2,2'-methylenebis-(4-hydrocarbyl-6-benzotriazolyl phenol) is preferably carried out in the presence of an alkaline catalyst. Examples of alkaline catalysts are lower alkali metal alcoholates, such as sodium methylate and sodium ethylate; alkali metal hydroxides, such as sodium hydroxide and potassium hydroxide; and alkali metal alkaline salts, such as potassium carbonate and sodium carbonate. The amount of the alkaline catalyst is not critical, and small amounts are usually sufficient. A preferred amount is within the range from 0.001 to 50 parts by weight, preferably from 0.01 to 8 parts by weight, per 100 parts of Mannich base.

The reactions can be carried out over a wide range of temperatures. A suggested range that is satisfactory in most cases is from about 20° C. to about 200° C., preferably from about 30° C. to about 150° C.

The following Examples represent preferred embodiments of the process of the invention.

EXAMPLE 1

Preparation of 2,2'-methylene-bis-(4-methyl-6-benzotriazolyl-phenol)

4-Methyl-6-benzotriazolyl-phenol 225 g, diethylamine 110 g, and paraformaldehyde 51.8 g were dissolved in 250 ml of butanol, and heated with stirring at reflux temperature (95° C. to 105° C.) for 24 hours. The solvent was vacuum distilled off, and 308 g of 2-diethylaminomethyl-4-methyl-6-benzotriazolyl-phenol Mannich base was obtained as residue. (Yield=99%)

This Mannich base, 7.8 g, was dissolved in 20 ml of xylene, and sodium methylate (28% methanol solution) 0.15 g was added. The solution was heated with stirring under reflux at 140° C. to 150° C. for 10 hours while a nitrogen stream was passed through the reaction mixture. The solvent was vacuum distilled off, and 6.1 g of crude product was obtained as residue. (Purity=91%; Yield=96%)

The crude product was recrystallized from xylene, and a pale yellow powder, 2,2'-methylene-bis-(4-methyl-6-benzotriazolyl-phenol melting at 285° C. was obtained.

EXAMPLE 2

Preparation of 2,2'-methylene-bis-(4-methyl-6-benzotriazolyl-phenol)

6.2 g of the Mannich base obtained in Example 1 and 4-methyl-6-benzotriazolyl-phenol 4.5 g were dissolved in 200 ml of xylene, and sodium methylate (28% methanol solution) 0.2 g was added. The solution was heated with stirring under reflux at 140°-50° C. for 10 hours with a stream of nitrogen. After distilling of the solvent, and recrystallizing the residue from xylene, the desired product 2,2'-methylene-bis-(4-methyl-6-benzotriazolyl-phenol) was obtained in 95% yield.

EXAMPLE 3

Preparation of 2,2'-methylene-bis-(4-(1,1,3,3-tetramethyl)butyl-6-benzotriazolyl-phenol)

2-Diethylaminomethyl-4-(1,1,3,3-tetramethyl)butyl-6-benzotriazolyl-phenol Mannich base was prepared using 4-(1,1,3,3-tetramethyl)butyl-6-benzotriazolyl-phenol by the same procedure as in Example 1. This Mannich base 37 g and 4-(1,1,3,3-tetramethyl)butyl-6-benzotriazolyl-phenol 25 g were dissolved in 60 ml of xylene, and sodium methylate (28% methanol solution) 3.1 g was added. The solution was heated with stirring under reflux at 140°-50° C. for 10 hours with a stream of nitrogen. After distilling of the solvent, and recrystallizing the residue from xylene, 55.2 g of the crude product was obtained. (Purity=93%; Yield=93%)

The crude product was recrystallized from n-heptane, and a white powder, 2,2'-methylene-bis-4-(1,1,3,3-tetramethyl)butyl-6-benzotriazolyl-phenol, melting at 200° C. was obtained.

EXAMPLE 4

Preparation of 2,2'-methylene-bis-(4-cumyl-6-benzotriazolyl-phenol)

2-Diethylaminomethyl-4-cumyl-6-benzotriazolyl-phenol Mannich base was prepared using 4-cumyl-6-benzotriazolyl-phenol by the same procedure as in Example 1. This Mannich base 10.0 g and 4-cumyl-6-benzotriazolyl-phenol 6.6 g were dissolved in 60 ml of xylene, and sodium methylate (28% methanol solution) 3.1 g was added. A white crystalline product, 2,2'-methylene-bis-(4-cumyl-6-benzotriazolyl-phenol) melting at 190° C. was obtained. (Yield=93%).

EXAMPLE 5

Preparation of 2,2'-methylene-bis-(4-methyl-6-benzotriazolyl-phenol)

31.0 g of the Mannich base obtained in Example 1 and methyl iodide 30 g were dissolved in 100 g of ethanol, and heated with stirring at reflux temperature (60° C. to 75° C.) for 24 hours. The solvent was distilled off, and the pale yellow crystalline product (methyl-diethyl-2-hydroxy-3-benzotriazolyl-5-methylbenzylammonium iodide) was obtained by recrystallization from ethanol.

This product 9.0 g and sodium methylate (28% methanol solution) 4.0 g were dissolved in 40 g of butoxyethoxyethanol, and heated with stirring at reflux temperature (160° C. to 170° C.) for 10 hours while a nitrogen stream was passed through the reaction mixture. The solvent was vacuum distilled off, and 6.1 g of crude product was obtained as residue. (Purity=91%; Yield=96%)

The crude product was recrystallized from xylene and the desired product, 2,2'-methylene-bis-(4-methyl-6-benzotriazolyl-phenol) was obtained in 95% yield.

The excellent yields obtained in the above Examples are to be contrasted with the yields when the process of *Chemical Abstracts* 77 62720h (1972) is used.

COMPARATIVE EXAMPLE A

Preparation of 2,2'-methylene-bis-(4-methyl-6-benzotriazolyl-phenol)

4-Methyl-6-benzotriazolyl-phenol 22.5 g, paraformaldehyde 2.5 g and conc-sulfuric acid 0.5 g were dissolved in 50 ml of xylene, and heated with stirring at reflux temperature (140° C. to 150° C.) for 20 hours. The solution was washed with water. When the solvent was distilled off, 22.8 g of a dark brown crude product was obtained.

The crude product contained only 16% of the desired product, 2,2'-methylene-bis-(4-methyl-6-benzotriazolyl-phenol), and most of the crude product was unreacted 4-methyl-6-benzotriazolyl-phenol.

COMPARATIVE EXAMPLE B

Preparation of 2,2'-methylene-bis-(4-(1,1,3,3-tetramethyl)butyl-6-benzotriazolyl-phenol)

4-(1,1,3,3-Tetramethylbutyl)-6-benzotriazolyl-phenol 32.3 g and paraformaldehyde 2.5 g were dissolved in 100 ml of methylene chloride, and 50 g of 80% sulfuric acid was added dropwise over one hour. The solution was stirred at room temperature for 12 hours. The sulfuric layer was separated, and the methylene-chloride layer washed with water and dried. The solvent was distilled off and 22.5 g of brown crude product was obtained.

The crude product was consisting of 4% of unreacted 4-(1,1,3,3-tetramethyl)butyl-6-benzotriazolyl-phenol, 31% of desired product, 2,2'-methylene-bis(4-(1,1,3,3-tetramethyl)butyl-6-benzotriazolyl-phenol), methylen-bis(benzotriazolyl-phenol) compounds free from one or two 1,1,3,3-tetramethylbutyl groups at the 4-position (dealkylation products) 52%, and 13% of other unknown compounds.

The yield of the desired product was 24%.

Having regard to the foregoing disclosure, the following is claimed as the inventive and patentable embodiments thereof:

1. A process for preparing 2,2'-methylene-bis-(4-hydrocarbyl-6-benzotriazolyl-phenols) having formula III:

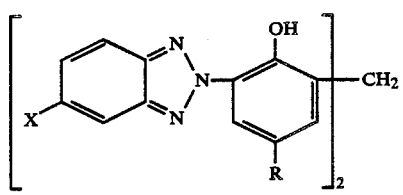

wherein:
R is selected from the group consisting of alkyl having from one to about twelve carbon atoms; arylalkyl having from seven to about fourteen carbon atoms and cycloalkyl having from three to about twelve carbon atoms;
X is selected from the group consisting of hydrogen, halogen, alkyl having from one to about twelve carbon atoms, aryl having from six to ten carbon atoms, arylalkyl having from seven to about sixteen carbon atoms, alkoxy having from one to about twelve carbon atoms, aryloxy having from six to ten carbon atoms; and arylalkoxy having from seven to about sixteen carbon atoms;
$R_1$ and $R_2$ are selected from the group consisting of hydrogen; alkyl having from one to about six carbon atoms, and $R_1$ and $R_2$ taken together to form a four to six member heterocyclic ring including a nitrogen atoms; provided, that at least one of $R_1$ and $R_2$ is not hydrogen; comprising (1) reacting a 4-hydrocarbyl-6-benzotriazolyl phenol having the formula I:

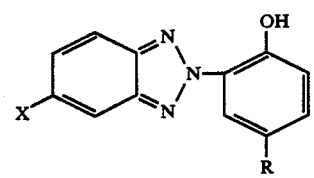

with an amine $HNR_1R_2$ and formaldehyde in an organic solvent to produce a Mannich base having formula II:

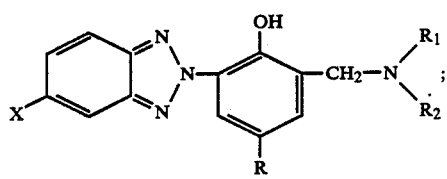

and (2) reacting the Mannich base with itself or a 4-hydrocarbyl-6-benzotriazolyl phenol having formula I, in the presence of an alkaline catalyst in an amount within the range from about 0.001 to about 50 parts by weight per 100 parts of Mannich base, thereby forming a 2,2'-methylene-bis-(4-hydrocarbyl-6-benzotriazolyl-phenol of formula III.

2. A process according to claim 1 in which $R_1$ is hydrogen and $R_2$ is alkyl.

3. A process according to claim 1 in which $R_1$ and $R_2$ are each alkyl.

4. A process according to claim 1 in which $R_1$ is hydrogen and $R_2$ is arylalkyl.

5. A process according to claim 1 in which X is hydrogen.

6. A process according to claim 1 in which X is halogen.

7. A process according to claim 1 in which X is alkyl.

8. A process according to claim 1 in which X is aryl.

9. A process according to claim 1 in which X is arylalkyl.

10. A process according to claim 1 in which X is alkoxy.

11. A process according to claim 1 in which X is aryloxy.

12. A process according to claim 1 in which X is arylalkoxy.

13. A process according to claim 1 in which the alkylidene bis-benzotriazolyl phenol is 2,2'-methylenebis(4-methyl-6-benzotriazolylphenol).

14. A process according to claim 1 in which the alkylidene bis-benzotriazolyl phenol is 2,2'-methylenebis(4-(1,1,3,3-tetramethylbutyl)-6-benzotriazolyl-phenol)).

15. A process according to claim 1 in which the alkylidene bis-benzotriazolyl phenol is 2,2'-methylenebis(4-cumyl-6-benzotriazolylphenol).

16. A process according to claim 1 in which the alkylidene bis-benzotriazolyl phenol is 2,2'-octylidenebis(4-methyl-(5'-methylbenzotriazolyl)phenol).

17. A process according to claim 1 in which the alkylidene bis-benzotriazolyl phenol is 2,2'-octylidenebis(4-methyl-(5'-chlorobenzotriazolyl)phenol).

18. A process according to claim 1 in which the reaction temperature in steps (1) and (2) is within the range from about 20° to about 200° C.

19. A process according to claim 1 in which the reaction temperature in steps (1) and (2) is within the range from about 30° to about 150° C.

20. A process according to claim 1 in which an inert organic solvent that is a solvent for the reactants is used in an amount within the range from about 50 to about 500% by weight of the benzotriazolyl phenol.

21. A process according to claim 1 in which the amounts of amine and formaldehyde in step (1) are within the range from about 0.5 to about 1 mole per mole of benzotriazolyl phenol.

22. A process according to claim 1 in which step (2) is carried out in the presence of an alkaline catalyst in an amount within the range from about 0.01 to about 8 parts by weight per 100 parts of Mannich base.

23. A process according to claim 1 in which the alkaline catalyst is a lower alkali metal alcoholate.

24. A process according to claim 1 in which the alkaline catalyst is a lower alkali metal hydroxide.

25. A process according to claim 1 in which the alkaline catalyst is a lower alkali metal alkaline salt.

* * * * *